United States Patent [19]

Moser

[11] Patent Number: 5,279,799

[45] Date of Patent: Jan. 18, 1994

[54] APPARATUS FOR CLEANING AND TESTING ENDOSCOPES

[75] Inventor: Hansruedi Moser, Magglingen, Switzerland

[73] Assignee: Hamo AG, Switzerland

[21] Appl. No.: 979,831

[22] Filed: Nov. 20, 1992

Related U.S. Application Data

[63] Continuation-in-part of Ser. No. 781,496, Oct. 22, 1991, abandoned.

[30] Foreign Application Priority Data

Oct. 23, 1990 [CH]  Switzerland .................. 03 386/90-4

[51] Int. Cl.⁵ ........................ A61L 2/00; A61L 9/00
[52] U.S. Cl. ................... 422/292; 134/102.2; 134/168 C; 134/170; 422/300; 422/905
[58] Field of Search ................... 134/166, 168 C; 134/170; 134/102; 422/28, 33, 422/292, 300, 905; 285/131, 137.1, 128, 920

[56] References Cited

U.S. PATENT DOCUMENTS

| | | | |
|---|---|---|---|
| 4,650,222 | 3/1987 | Cetrone | 285/137.1 |
| 4,860,638 | 8/1989 | Hosono et al. | 285/133.1 X |
| 5,139,287 | 8/1992 | Broere | 285/26 |

*Primary Examiner*—Robert J. Warden
*Assistant Examiner*—Krisanne M. Thornton
*Attorney, Agent, or Firm*—Ostrolenk, Faber, Gerb & Soffen

[57] ABSTRACT

An apparatus for cleaning and testing endoscopes by injecting pressurized air into the sheath and pressurized air and washing liquid into the ducts, and monitoring the same. A washing chamber is provided which contains retractable cages to hold the endoscopes during cleaning and testing. The cages include a coupler for detachably connecting tubes supplying the air and washing liquid to the endoscopes. The cages also have markings for automatically activating the apparatus when a cage containing an endoscope is inserted into the washing chamber.

9 Claims, 3 Drawing Sheets

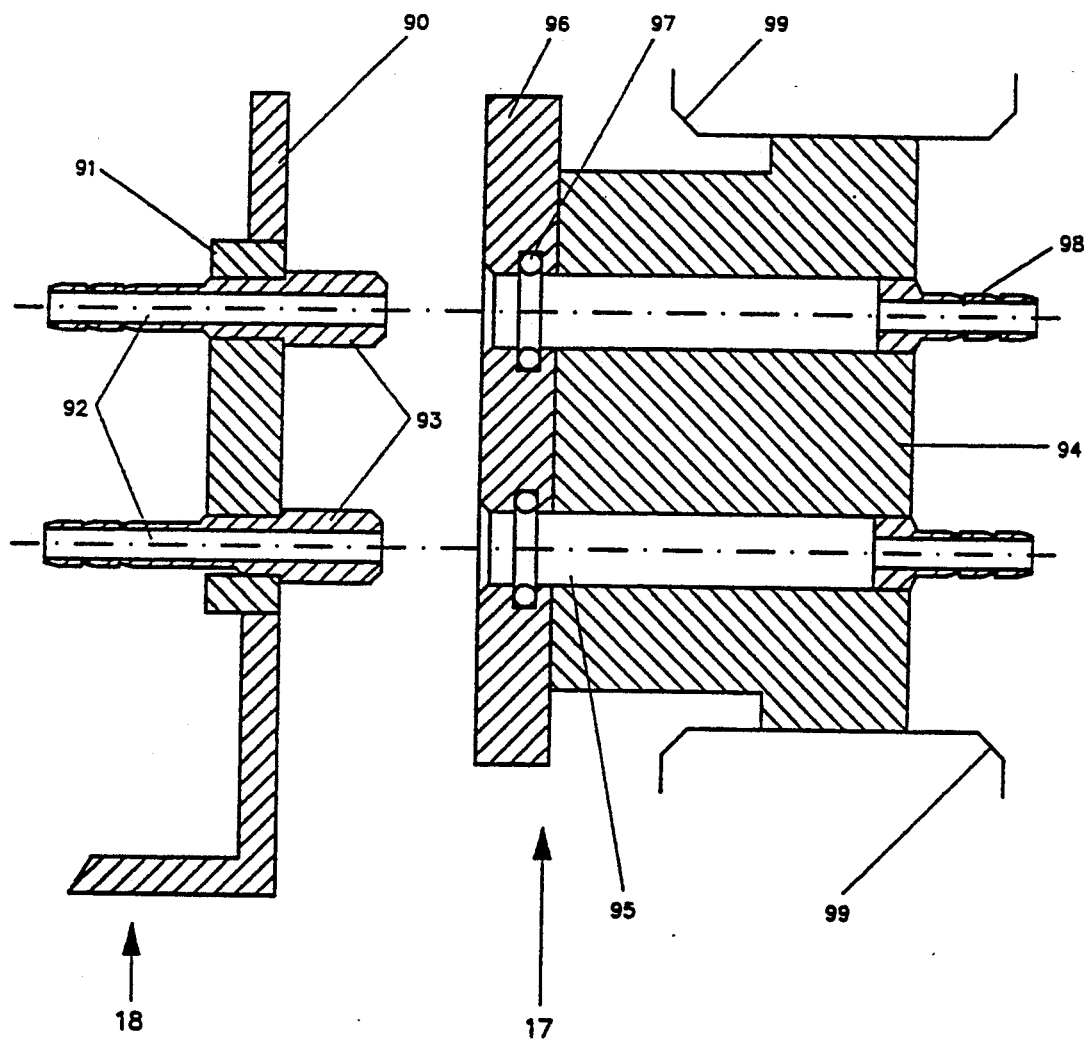

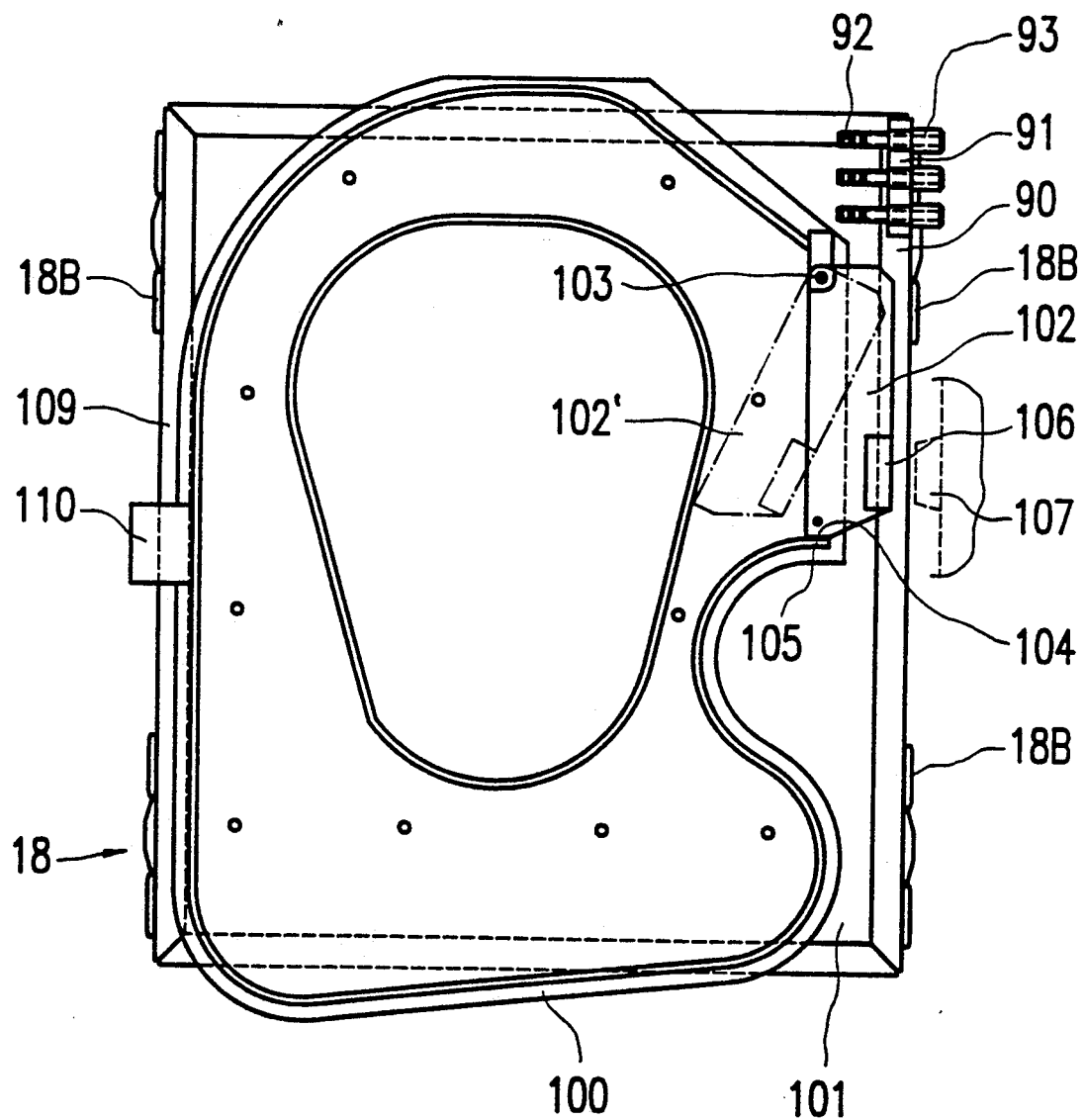

APPARATUS FOR CLEANING AND TESTING ENDOSCOPES

This is a continuation-in-part application of Ser. No. 07/781,496, filed Oct. 22, 1991 now abandoned.

BACKGROUND OF THE INVENTION

The present invention relates to a new and useful apparatus for cleaning tubular articles, in particular those used in chemical, medical, biological and other laboratories, and in numerous other fields such as medicine, space technology, nuclear technics, etc. The apparatus is particularly useful for cleaning endoscopes, preferably gastroscopes, i.e. stomach endoscopes. The cleaning operation as contemplated includes disinfecting and drying of the tubular articles.

Endoscopes are devices for viewing and monitoring the interior of cavities of human and animal bodies and often allow, in addition, the taking of tissue samples (biopsy) from the body. Endoscopes are tubular, flexible optical devices which are normally introduced into the body through a natural opening therof so that a local inspection of the body cavity may be made. The particular endoscope used is adapted to the anatomical conditions of the body. A light source is incorporated into the endoscope at the leading end of a tubular, flexible shaft, and a mechanism for the movement of the endoscope head is mounted at the other, outer end of the endoscope. The image produced by the light source is conducted to an outer ocular by a light conductor, such as a fiber optic. In addition, endoscopes have several ducts or conduits for the supply and recovery of stomach or other liquids, the supply of contrasting agent, etc. All these ducts are incorporated into the tubular sheath or shaft.

Endoscopes are very expensive instruments which cannot be discarded after use but have to be cleaned, disinfected and/or sterilized.

The cleaning of the fine ducts in the endoscope is difficult. A simple rinsing is not sufficient if the ducts are clogged. Moreover, sometimes the outer shell or sheath is damaged and leaks. Finally, the correct drying of the ducts is difficult to do as well.

A washing machine disclosed in German Patent No. DE-C2-3,143,005 for cleaning laboratory and hospital articles, especially hoses, comprises the following main parts:

a machine body having a washing chamber, a collecting pool for washing liquor, a circulating pump and rotating spray arms, all these parts being known from conventional dish washing machines, and a retractable cage for receiving said tubular articles;
connection means for removably connecting said tubular articles to supply tubes for washing liquor; and
means for programming and controlling the washing cycle.

A cleaning apparatus for elongated devices, e.g. endoscopes, is disclosed in U.S. Pat. No. 4,763,678 (Ott). Surprisingly, the Ott apparatus can only clean endoscopes which are attached to the free outside of the cleaning apparatus, and the mandatory sterilization of an endoscope can therefore not be performed. Cleaning hoses are attached to the endoscope by a manually operated coupling device which is not shown nor described in the patent. There is no carriage to receive the endoscope and to introduce it into a washing chamber.

U.S. Pat. No. 4,299,244 (Hirai) describes an endoscope washing apparatus where the endoscope to be washed is submerged in flowing water. Washing liquor is also admitted to the channels of the endoscope but the connector unit is not described. There is no carriage to receive the endoscope and to introduce it into a washing chamber.

U.S. Pat. No. 4,216,767 (Aoshiro) merely describes an endoscope and a general method for washing and testing the channels of the instrument but fails to disclose a washing apparatus.

Finally, U.S. Pat. No. 4,975,245 (Archer et al.) discloses a hot air sterilization device having a removable tray to support the instruments to be sterilized. However, since medical instruments having internal ducts are not mentioned for sterilization, the problem of connecting such instruments to the sterilization device is not concerned.

A major objective of this invention is to provide a washing machine that improves the known machine in several respects and allows a better, more secure, and highly automated operation.

SUMMARY OF THE INVENTION

Accordingly, an object of the present invention is to provide a washing machine of the chamber-carriage type for tubular articles offering an absolutely reliable disinfecting and drying of the duct or ducts of said tubular article.

An important object of this invention is to provide said washing machine with automatic programming devices so that the machine may intelligently discover the presence or the absence of an inserted endoscope and select the testing and washing program.

Another important object of the invention is to provide said washing machine with means for testing the sheath for leakage and the duct or ducts of said tubular article for blockage.

Still another object is to provide said machine with means for a perfect cleaning and disinfecting of the outer surfaces of said tubular article.

To fulfill these objectives, and still others, the apparatus of the present invention, comprises first means for testing the sheath of a tubular article received in a cage or cages contained in the washing machine, the leakage test being executed periodically during the operation of said cleaning program, second means for testing the individual ducts in said tubular article for blockage, and third means for improving the effectiveness of the cleaning by supplying pneumatic pressure pulses to said ducts, further comprises fourth means for automatically connecting the articles to be cleaned with the above enumerated means and means for automatically selecting washing programs.

The first means, i.e. the leakage testing means for the sheath, preferably comprises the following parts: An automatically controlled pneumatic pressure reducing valve having a device for keeping a preselected gas pressure on the low pressure output constant, i.e. on the delivery side; a magnet (solenoid) valve to be operated periodically; a first pressure switch sensitive to any excess pressure over said preselected pressure, as well as a second pressure switch sensitive to any depression under said preselected pressure; and a conduit to connect said preselected pressure to the sheath space of the article to be cleaned.

The second means, i.e. the means for testing flow through the individual ducts, generally comprises a gas pressure reducer for supplying a predetermined test pressure, normally an air pressure; a test valve to be opened and closed in intervals for testing the free flow of the pressurized gas through the ducts of the article; a pneumatically operated stop valve to isolate washing liquid from said ducts when they are being tested for free flow; controllable valves, preferably magnetically operated squeezed tube valves, in lines leading to any one of the ducts; and a free flow sensor, preferably a float body magnet switch, in a line leading to any one of said ducts.

The third means comprises a pneumatically operated stop valve which is periodically opened and closed, and which injects pressurized air into a line containing the washing liquid during the cleaning cycle in order to inject air into the ducts for improving the cleaning operation.

The fourth means of the invention comprise a connector mounted in a wall of the cage or cages and a coupling block mounted at the inside of each washing chamber, these two parts being in alignment when the cage is in its innermost operating position, and means on the retractable cage for detecting the presence of an inserted endoscope cooperating with sensors at the inside of each washing chamber.

The particular design of said two connecting parts and of said detector means is described below. They serve to automatically connect the ducts of the tubular article to the lines supplying air and cleaning liquor. The retractable cage further comprises control means mounted on a pivotable flap, and the machine comprises cooperating detector means for sensing the presence or the absence of an endoscope laid into the cage in cleaning position, i.e. the washing machine is automatically informed whether there is an endoscope in the cage or not. This is important since endoscopes comprise cemented locations where the cement does not withstand temperatures above 50° C., and the machine is thus prevented by the action of the control means from running a program applying higher temperatures. Furthermore, the control means may be arranged to transmit other program information to the machine. This is achieved by different flaps to be exchanged against the operating flap. Details will be described later.

The apparatus may further contain a fifth means for controlling and metering the flow of at least one cleaning liquid to be supplied to the article to be cleaned.

Other features and advantages of the present invention will become apparent from the following description of a preferred embodiment which refers to the accompanying drawings.

BRIEF DESCRIPTION OF THE DRAWINGS

FIG. 2 represents a longitudinal section of a coupling device for coupling the ducts to be cleaned to the supply lines of air and liquid; and FIG. 3 shows a top view of a retractable cage 18.

DESCRIPTION OF THE EMBODIMENTS OF THE INVENTION

Figure 1:
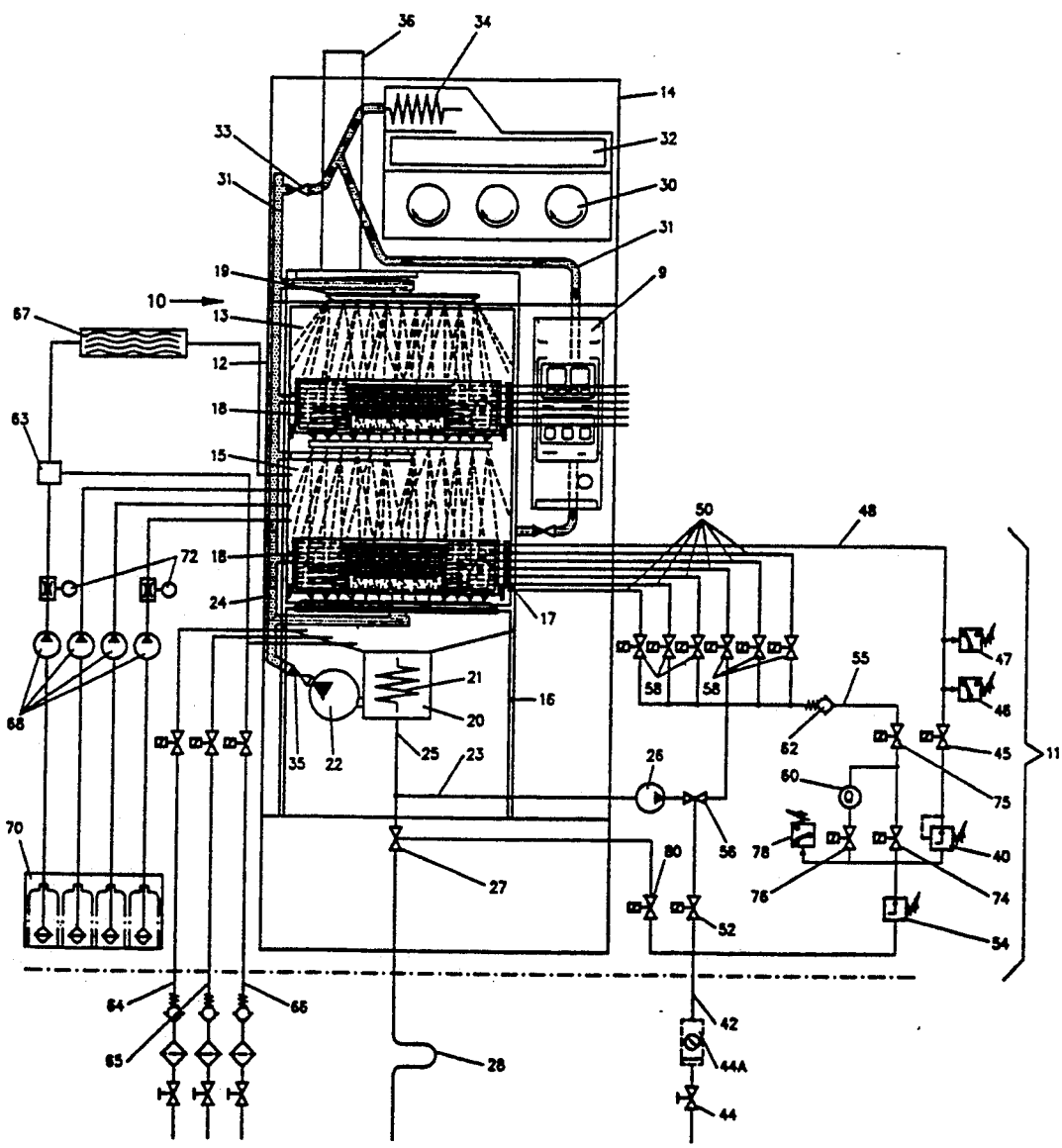
FIG. 1 shows a schematical design of a cleaning machine of the invention.

Referring to FIG. 1, the cleaning machine comprises a cleaning machine body 10 which is divided into three vertically superimposed main sections: a center section 12, which embodies the actual cleaning chamber, an upper section 14 and a lower section 16.

The center section 12 is formed of one or more substantially identical chamber portions 13 and 15 in which cages 18 are accommodated containing the endoscopes to be cleaned. The endoscopes are introduced on the retractable cages into the center section 12 from the front side. The cages 18 have wheels 18B, shown in FIG. 3, which run on rails 18A fixed at the lateral inner sides of the chamber portions 13, 15. Spraying arms 19 are provided in a basically known manner. Furthermore, electronic control unit 9 is laterally attached to said center portion 12. Said control unit 9 comprises an operating and display panel 9A that monitors the operation of the machine as well as possible disturbances. Control unit 9 contains all the installations which are necessary for the control and supervision of the operating procedure, including a microprocessor.

The cleaning liquid which is sprinkled by spraying arm 19 arrives at the lower section 16 where it is collected in a pool 20 which is provided with a heating element 21 in order to reheat the liquid. By means of a circulating pump 22, said cleaning liquid is redelivered under pressure to the spraying arms 19, and other, stationary spraying nozzles through tube 24.

In contrast to the known devices in which duct 24 is provided with a simple branch and comprises further pressure pumps for the internal cleaning of the endoscope channels (described herebelow), namely one such pump for each channel, according to the present invention, a duct 23 bifurcates from pool 20, i.e. from drain 25 to a common rinsing pump 26.

Furthermore, in the lower machine section 16, valves, regulators and other devices are accommodated which are generally referenced by 11 and described below. These parts are shown in FIG. 1 in lateral relationship to the lower machine section 16; in reality, they are of course arranged within said section 16. Moreover, a solenoid-controlled draining valve 27 is interposed in drain 25 whereby the discharge of the cleaning liquor to siphon 28 is controlled.

Fans 30 for dry air are accommodated in the upper section 14, said dry air being forced through a fine filter 32 and across an air heater 34 into tubes 31 when the air valve 33 is open and the valve 35 (in lower section 16) of circulating pump 22 is closed to carry out the drying phase.

The cages 18, each of which receives an endoscope, are preferably designed as boxes having a pivotable and removable, lateral flap 102. These boxes may be closed, i.e. having water-tight bottom and walls, or they may be designed as cages where the bottom and walls are formed of grids. The first embodiment allows to submerge an endoscope in cleaning fluids. Internally, the cages 18 are provided with pipe stems 92, on each of which a connecting tube of the channel of the endoscope to be cleaned is plugged. Said stems are shown in FIGS. 2 and 3. How the cage is constructed and how the connection to the rinsing lines is established will be described below.

Said cages 18, when constructed as closed boxes, will allow a complete external cleaning of the endoscopes, namely by total immersion ("soaking"). However, a drain is provided as well, so that each cage 18 is emptied quickly at the end of every rinsing cycle.

The installations shown as 11 are now discussed in more details.

The first group of additional installations refers to the periodical pressure test of the external sheathing of the endoscope. It has been found that said endoscope sheath (not shown) may be exposed to a maximum inside pressure of 0.2 bar.

The heart of the pressure testing device for the leakage test of the endoscope sheath is an automatic pressure reducing valve 40. The latter is connected through a pressure reducing valve 54 for channel testing to a compressed-air duct 42 which is connected to a compressed-air source (not shown), e.g. of 2.5 bar, via manintenance unit 44A and stop valve 44. Pressure reducing valve 40 maintains the nominal pressure, e.g. 0.2 bar, in supply line 48, excess pressure being released. A solenoid valve 45 is connected after automatic pressure reducer 40. Said valve, and also the remaining active component parts of the auxiliary installations 11, are linked to control/monitoring and programming unit 9 by non-represented connections which will not always be mentioned hereinafter.

Furthermore, two pressure switches 46 and 47 are mounted in line 48 which leads to the connector for the endoscope sheath, one pressure switch, e.g. 47, being sensitive to a pressure below the testing pressure, and the other, 46, responding to a pressure above the testing pressure.

As an example, the control unit 9, and the arrangement of parts, 40, 45, 46, 47, 48, operate as follows (durations and pressures serving merely as examples):

It is assumed that the nominal pressure (testing pressure) amounts to 0.18 bar, and the lower switching pressure to 0.16 bar. At first, solenoid valve 45 opens for 3 seconds. The testing pressure of 0.18 bar, regulated by regulator 40, builds up in line 48 and in the sheath of the endoscope, which forms a closed space. Solenoid valve 45 is the closed again.

If the sheath is tight and the endoscope is warmed up in the cleaning machine, the pressure in the sheath will rise. Should it attain 0.20 bar, valve 45, prompted by switch 46, will open, and regulator 40 provides for a reduction of the pressure to 0.18 bar. If the sheath is tight and the endoscope is cooled in the cleaning machine (admission of cold water or cold high-purity water), the pressure in the endoscope sheath will drop. As long as the admission valve for cold water of high-purity water is open (lines 64 and 66, respecively), and the pressure consequently drops below 0.16 bar, valve 45, prompted by switch 47, will open for 2 seconds, and regulator 40 provides for a pressure rise to 0.18 bar.

If the endoscope sheath or one of the ducts of the device is leaking, the pressure will drop, and if the pressure drops below 0.16 bar, switch 47 will trigger an alarm and the cleaning machine will be stopped. This phase of the pressure test lasts for e.g. 3 minutes, whereupon the described cycle is repeated during the entire rinsing cycle. It is thus ensured that no water can enter the endoscope, and that it may be repaired if necessary.

The indicated pressure and limit values as well as the durations may of course be selected at will and adapted to the requirements.

Additional lines 50—normally three to seven—which are shown in FIG. 1 are connected to the corresponding ducts of the endoscope by an automatic connector 17 which is described hereinafter. Contrary to the sheath, these ducts are open; in this case it is not a tightness test but a passage test that is required and carried out, namely by means of air before and after washing and rinsing.

For this purpose, a pressure reducer 54 is provided in high purity air line 42. Valve 52 causes a stop valve 56 after duct rinsing pump 26 in rinsing line 23 to close, and, therefore the following parts of the apparatus are not supplied with cleaning liquor.

After stop valve 56, rinsing line 23 branches into several valves 58 which open or close lines 50 leading to the endoscope ducts. According to a further characteristic of the invention, said valves are sqeezed tube valves which are anti-soiling and self-cleaning and which are driven by powerful magnets.

For the passage test of the endoscope ducts, valve 74 is closed and valve 76 is opened. If the connected endoscope duct is not clogged, air flows through the endoscope duct via float body magnet switch 60 which is mounted in the test line, valves 75 and 62 and the corresponding duct valve 58. The tested duct is then disconnected by closing valve 58, and another duct is tested. If a given duct is clogged, magnet switch 60 is not released, the clogged duct is indicated on a display field of control unit 9, and the machine is stopped.

After the free flow test, the cleaning operation may begin, which is not basically different from known methods. As usual, several programs are provided and selectable.

First, according to the program, cold water, warm water or high-purity water (the latter only for final rinsing) are supplied to the lower section of the machine through lines 64, 65 and 66 and heated by heater 21 in pool 20 if necessary. Circulating pump 22 forces the cleaning liquor into spraying arms 19 and into other, stationary spraying devices. The addition of detergent, neutralizing agent, so-called instrument milk, and disinfectant is effected by means of pumps 68 which pump the corresponding liquids from a container battery 70 to center section 12 of the cleaning machine where they are mixed to the circulating rinsing water. The flow of some or of all additives is monitored and, if necessary, measured by means of flow detectors 72. Generally, however, it is sufficient to dose the necessary quantities of additives by timing the pumps 68 which are designed as metering pumps.

The disinfectant, which is pumped from the battery of bottles 70 shown at the very left of FIG. 1, is not supplied to the cleaning machine directly but in the form of a ready-to-use, aseptic, diluted solution. For this purpose, a mixing point 63 is provided which is supplied with concentrated disinfectant, on one hand, and with highly purified water from line 66, on the other. After mixing the two liquids, whose mixing ration may be made adjustable and controllable, the diluted solution is supplied to an aseptic filter 67, said filter being described in a non-published suggestion.

A membrane filter permitting a high water flow is preferably used for aseptic filter 67. It is particularly advantageous to use High-Flux industrial filters, as are used for aseptic filtration in usual hemodialysis. On account of their material properties, such filters are hydrophilic and are made e.g. of polyvinyl pyrrolidonehydrophilised polysulfone, acetyl cellulose, polyacrylonitrile or the like. Usually, they have a membrane surface area comprised between 1 and 3 $m^2$ and are available in the form of a hollow fiber filter containing about 9,000 to 10,000 hollow fibers in a substantially cylindrical housing. Such hollow fiber membranes have an internal diameter of about 0.2 mm, a wall thickness of about 20 to 30 $\mu$m and an average pore size below 0.5 $\mu$m, more particularly below 0.1 $\mu$m.

The device of the invention thus has the advantage that the aseptic filter 67, which is disposed in front of the rinsing chamber 15, positively prevents introduction of germs into said rinsing chamber, and all appliances which have been treated with liquid disinfectant in the cleaning machine remain positively aseptic even after rinsing with aseptic fresh water, as is obtained on the delivery side of the aseptic filter.

In the cleaning programs, the exterior of the endoscope is not only sprayed but, since the cages 18 generally have solid sides and bottoms, it is completely immersed in cleaning liquid. This is an important advantage of the invention when endoscopes have to be rehydrated.

Simultaneously, the endoscope ducts are cleaned by opening all the duct valves 58 while pump 26 is supplying the cleaning liquid through line 23, valve 56 being open. Valve 52 is periodically opened, wherby valve 56 is caused to close against pump 26, and a compressed-air pulse is applied to the endoscope ducts via line 55, valves 58 and lines 50. These periodical compressed-air pulses substantially contribute to the cleaning of the ducts.

After every cleaning operation, i.e. generally prewashing, washing, disinfection, final rinsing and possibly drying, the endoscope ducts are blown out in order to be emptied. For this purpose, air valves 74 and 75 are opened while valve 56 is closed. The connected pressure reducer 54 reduces the air pressure to a suitable value; valve 75 is closed by a pressure switch 78 if an excessive pressure should build up in line 55. Normally, all duct valves 58 are open during the blow-out operation.

At the end of every cleaning cycle, the cleaning liquid can be discharged by pneumatically operated valve 27 (controlled by air valve 80).

External drying of the endoscope is effected by filtered warm air which is blown into the machine by fans 30, passing through filter 32 and heater 34, and then through lines 31. The exhaust air escapes through tube 36.

It should be noted that the endoscope sheath is tested for leakage during the entire cleaning procedure, as has been described in detail above.

In the drawing, FIG. 2 schematically shows a longitudinal section of a portion of cage 18 and of connector (or coupling device) 17.

Into the rear area of a lateral wall 90 of cage 18 (or in the rear wall of said cage), a connecting piece 91, e.g. of circular section, is tightly inserted. Said connecting piece 91 is pierced, and on the inside of cage 18, the bores are terminated by hose stems 92 to which the ducts of the endoscope to be cleaned (not shown) are connected. On the outside, straight, smooth stems 93 preferably having rounded front sides are provided. The numer of bores with stems 92 and 93 is adapted to the number of endoscope ducts, including sheath; that is at least one and generally seven, as illustrated in FIG. 1 (lines 48 and 50). In FIG. 2, only two connections are shown for the sake of simplicity.

A coupling device 17 matching connecting piece 91 is disposed in center section 12 of cleaning machine 10. Said coupling device is placed in such a manner that a direct, reliable, tension-free connection with connecting piece 91 is established by lateral displacement of coupling device 17 when cage 18 is correctly inserted into the machine, said connection being effected automatically when sensors (not shown) signal a correct end position of inserted cage 18.

Coupling device 17 is formed of a cylindrical block 94 which comprises the same number of bores 95 as stems 93 are provided on cage 18. In the end position of cage 18, bores 95 are aligned with stems 93. Bores 95 end in a front disk 96 of block 94 where suitable sealing means for the associated stems 93 are provided, for example O-ring joints 97 made of a self-lubricating material. The rear side of block 94 is again provided with hose stems 98 prolonging bores 95 and serving for the connection of lines 48 and 50 (FIG. 1). The circumference of block 94 which is capable of reciprocating in the direction of arrow 99A is designed as a double-action pneumatic piston and cooperates with a schematically illustrated pneumatic cylinder 99. Elements which are not directly necessary for the understanding of the construction, such as guides and the rotational securing of block 94, stops for stroke limitation, connections, sensors, etc. are not shown. Front disk 96 may also be integral with block 94.

One cage 18 for receiving the endoscope and for the insertion into the middle section 12 of cleaning apparatus 10 is shown as a top view in FIG. 3. The cage 18 has a generally rectangular outer shape. Wheels 18B are provided at the corners of that general rectangle; these wheels serve, as already mentioned above, as guide and roller means to insert the cage or cages 18 into the endoscope washing mashine where they run on corresponding horizontal rails 18A. An endoscope receiving, closed-loop wall 100 is fixed on the rectangular bottom 101 of the cage 18; this closed-loop wall 100 is adapted to the shape of endoscopes and allows to perfectly accomodate an endoscope (not shown) together with its control and viewing devices.

In the neighborhood of the connector block 91, the wall 100 is interrupted and closed by a flap 102 which is pivotable around a vertical hinge pin 103. The shape of the flap 102 is adapted to the opening in the wall 100; when the flap 102 is closed (shown in full lines in FIG. 3), the inner space surrended by the wall 100 is substantially closed whereas, when the flap 102 is open as shown as 102' in FIG. 3, wall portions 104 of the flap and 105 of the closed-loop wall 100 are no longer in contact.

A control device 106 is incorporated into the outer portion of the flap 102. When the cage is completely and correctly inserted into the endoscope washing machine, the control device 106 alignes and cooperates with a detector device 107 attached to the inner wall of the cleaning compartment 13 of the endoscope washing machine. In the simplest embodiment, this control device 106 is a permanent magnet, and the detector device 107 is a magnetic detector which detects the absence or the presence of a magnet. However, the invention prefers a more complex system which not only detects the absence or the presence of a closed flap but also the type of endoscope put into the cage 18; for example, this may be achieved by providing different flaps 102 having more than one magnet, arranged in different mutual space relationship or having different magnetical strength. The particular, desired flap will be selected when a particular endoscope is introduced into the cage, and the change of the flap will easily be made by simply lifting the pin 103, removing the "old" flap, and inserting the desired one. The detector device 107 should of course be able to detect the corresponding arrangement pattern of the control device 106. The particular construction of the devices 106 and 107 will not be described in detail since such constructions are within the knowledge of the one skilled in electronic art.

When an endoscope is inserted into the cage 18, namely into the inner space delimited by the closed-loop wall 100, the flap 102 must be pivoted into its closed position; otherwise, an endoscope cannot be inserted. The flap 102 is thus in its operating position; when the cage 18 is pushed home into the washing machine, the control device 106 on the closed flap will face the detector device 107. Any desired or appropriate washing or sterilizing program will then automatically be initiated. It is known in particular that endoscopes must not be subjected to temperatures exceeding about 50° to 60° C. The cooperation between the control and detector devices 106 and 107 will prevent a program using higher temperatures from running.

In contrast thereto, when no endoscope is inserted into the cage and other instruments are in the cage, e.g. rubber hoses or glass instruments, or even if the cage is empty, the flap 102 is in inoperating position with regard to the detector 107, and other programs using for instance higher temperatures, may be run.

The facing wall 109 of the cage is equipped with a water trap 110 which is not essential for the invention.

Operation of the coupling device 17 of FIG. 2 is as follows. After correct insertion of cage 18 in machine 10, stems 93 are aligned with bores 95. After activation of corresponding detectors (not shown), pneumatic cylinder 99 will displace coupling device 17 towards the left in FIG. 2 (and 1) until front disk 96 abuts to cage wall 90. In the process, stems 93 enter bores 95 and are sealed by O-rings 97.

The washing machine may be programmed as follows. Once the coupling connection is established as described above, the machine operator will push the start bottom. If an endoscope had been inserted into the cage, the basic endoscope cleaning program will be ready to be run. If no endoscope had been inserted, there will be no interacting connection between the control 106 and the detector 107, and an error message "No endoscope in cage" will be displayed on display device 9A when an endoscope cleaning program is selected. However, other, non-endoscope cleaning programs can be run.

After the cleaning and drying of the endoscope ducts is completed, coupling device 17 is automatically retracted, namely substantially to the position shown in FIG. 2, and cage 18 can be withdrawn from machine 10.

It has already been mentioned above that parts and operations may be replaced with other, suitable ones. The invention is not limited to what has actually been described in the example, but it may be modified by a person skilled in the art within the scope of the claims without detriment to its protection. Thus, for example, the stems of the connecting piece according to FIG. 2 and the bores of the coupling block may be mutually exchanged. The connecting elements of the coupling block may be threaded connections, etc.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

I claim:

1. An apparatus for cleaning and testing endoscopes having an outer flexible sheath and one or more longitudinal ducts, comprising:

(a) a washing chamber containing at least one retractable cage for receiving an endoscope;
   (b) first testing means for testing a sheath of an endoscope operatively disposed in said cage for leakage, including means for injecting pressurized air into a sheath of an endoscope operatively disposed in said cage and monitoring the pressure of said injected air;
   (c) second testing means for testing ducts of an endoscope operatively disposed in said cage for blockage, including means for injecting pressurized air into ducts of an endoscope operatively disposed in said cage, and monitoring the pressure of said injected air;
   (d) additional means for automatically connecting said first and second testing means to a sheath and ducts, respectively of an endoscope operatively disposed in said cage, when said retractable cage containing an endoscope is inserted in said washing chamber; and
   sensor means inside said chamber and further means on said retractable cage for cooperating with said sensor means to detect the presence of an endoscope within said cage.

2. The apparatus according to claim 1, wherein said second testing means includes means for cleaning said ducts by periodically injecting pressurized air with washing liquid into said ducts.

3. The apparatus according to claim 1, wherein said means for automatically connecting said first and second testing means comprises:

(a) a connector mounted in said retractable cage, said connector comprising a first and a second hose coupling inside said retractable cage for connecting with an endoscope operatively disposed in said cage, a first and a second straight stem outside said retractable cage and aligned with said first and said second coupling, respectively, and a first bore passing through said first hose coupling and said first stem, and a second bore passing through said second hose coupling and said second stem;
   (b) a coupling block mounted in said washing chamber having a first and a second bore aligned with said first and said second stem, respectively, when said retractable cage is in an operating position, said first and said second bore of said coupling block each having at one end a sealing means to seal said bore to said straight stem entered therein, and at the opposite end a connecting means to connect said bore to said first and second testing means; and
   (c) a pneumatic cylinder for moving said coupling block horizontally towards and away from said straight stem, for respectively coupling and detaching said bores of said coupling block in relation to said straight stems.

4. The apparatus according to claim 1, wherein said further means comprises a control device and said sensor means comprises at least one detector device for sensing the vicinity of said control device, said control and said at least one detector devices being operatively aligned when said cage is in an operating position and being arranged to enable or disable the running of a particular washing program.

5. The apparatus according to claim 4, wherein said retractable cage further comprises a lateral flap which pivots about a vertical axis into said retractable cage when said cage does not contain said endoscope, but is prevented from opening when said endoscope is inserted in said retractable cage, said control device being fixed to said flap and being operatively positionable to interact with said at least one detector device when said endoscope is inserted into said retractable cage and said flap is closed, and being inoperative to interact with said sensors when said retractable cage is empty and said flap is open.

6. The apparatus according to claim 4, wherein said control device is at least one magnetic mark.

7. The apparatus according to claim 6, wherein said detector device comprises several magnetic marks having different magnetic strength or being arranged in a predetermined pattern in order to transmit complex information to said control device.

8. The apparatus of claim 5, wherein said cage has a generally rectangular bottom shape and comprises a closed-loop upright wall being shaped to receive the shape of an endoscope that is coiled, said flap closing a lengthwise opening of said upright wall, the flap being pivotable around a vertical pivot pin and closing said lengthwise opening when an endoscope is inserted into said cage.

9. The apparatus of claim 8, wherein said flap is removably journalled by said pivot pin which is removable, the flap being exchangeable with another flap having a differently designed control device.

* * * * *